US009550689B2

(12) United States Patent
Grossman

(10) Patent No.: US 9,550,689 B2
(45) Date of Patent: Jan. 24, 2017

(54) FLUID FILTRATION APPARATUS

(71) Applicant: Allied Bioscience, Inc., Dallas, TX (US)

(72) Inventor: Craig Grossman, Point Roberts, WA (US)

(73) Assignee: ALLIED BIOSCIENCE, INC., Dallas, TX (US)

( * ) Notice: Subject to any disclaimer, the term of this patent is extended or adjusted under 35 U.S.C. 154(b) by 481 days.

(21) Appl. No.: 14/217,112

(22) Filed: Mar. 17, 2014

(65) Prior Publication Data

US 2014/0286843 A1    Sep. 25, 2014

Related U.S. Application Data

(60) Provisional application No. 61/786,306, filed on Mar. 15, 2013.

(51) Int. Cl.
| | | |
|---|---|---|
| *A61L 2/00* | (2006.01) | |
| *C02F 1/72* | (2006.01) | |
| *A61L 9/00* | (2006.01) | |
| *B01D 61/22* | (2006.01) | |
| *C02F 1/30* | (2006.01) | |

(Continued)

(52) U.S. Cl.
CPC .............. *C02F 1/725* (2013.01); *A61L 2/00* (2013.01); *A61L 9/00* (2013.01); *B01D 61/22* (2013.01); *C02F 1/30* (2013.01); *B01D 71/024* (2013.01); *B01D 2325/40* (2013.01); *B01D 2325/44* (2013.01); *C02F 1/32* (2013.01); *C02F 2101/322* (2013.01); *C02F 2201/3224* (2013.01); *C02F 2209/40* (2013.01); *C02F 2305/10* (2013.01)

(58) Field of Classification Search
CPC ............ A61L 2/088; A61L 9/205; A61L 2/00; A61L 9/00; A61L 2/08; A61L 9/20; C02F 1/725; C02F 1/30; C02F 1/32; C02F 2101/322; C02F 2305/10; C02F 2201/3224; C02F 2209/40; C02F 1/72; B01D 61/22; B01D 71/024; B01D 2325/40; B01D 2325/44
See application file for complete search history.

(56) References Cited

U.S. PATENT DOCUMENTS 5,875,384 A * 2/1999 Peill ....................... B01J 19/123
422/186
6,501,893 B1   12/2002 Iimura
(Continued)

FOREIGN PATENT DOCUMENTS

| JP | 11342315 A | 12/1999 |
|---|---|---|
| JP | 2005200275 A | 7/2005 |

OTHER PUBLICATIONS

PCT/US2014/030767—International Search Report and Written Opinion dated Sep. 3, 2014.
(Continued)

*Primary Examiner* — Walter D Griffin
*Assistant Examiner* — Cameron Allen
(74) *Attorney, Agent, or Firm* — Snell & Wilmer L.L.P.

(57) ABSTRACT

A fluid filtration apparatus, which includes a plurality of optical fibers each having a length, wherein one or more of the plurality of optical fibers exhibits frustrated total internal reflection, thereby emitting light along the length of one or more of the optical fibers, in combination with a photocatalyst disposed on the plurality of optical fibers and a light source interconnected to the plurality of optical fibers.

16 Claims, 9 Drawing Sheets

(51) Int. Cl.
C02F 1/32 (2006.01)
C02F 101/32 (2006.01)
B01D 71/02 (2006.01)

(56) References Cited

U.S. PATENT DOCUMENTS

| | | |
|---|---|---|
| 2008/0308405 A1 | 12/2008 | Yu et al. |
| 2010/0209294 A1* | 8/2010 | Owen .................... A61L 9/205 422/24 |
| 2012/0228236 A1 | 9/2012 | Hawkins et al. |
| 2014/0110351 A1* | 4/2014 | Fahs, II .................... C02F 1/32 210/748.11 |

OTHER PUBLICATIONS

PCT/US2014/030767—International Preliminary Report on Patentability dated Sep. 24, 2015.

* cited by examiner

222

232

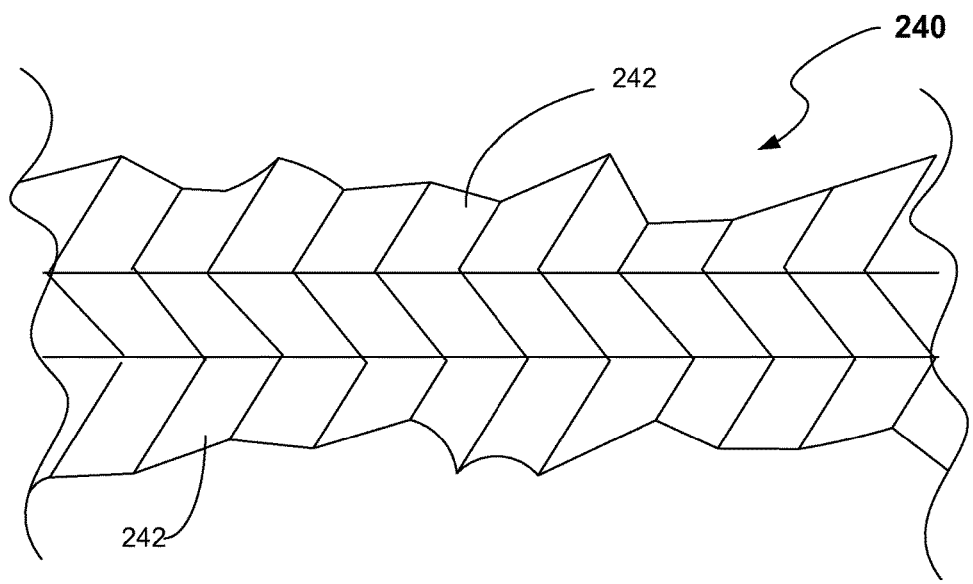
FIG. 2E
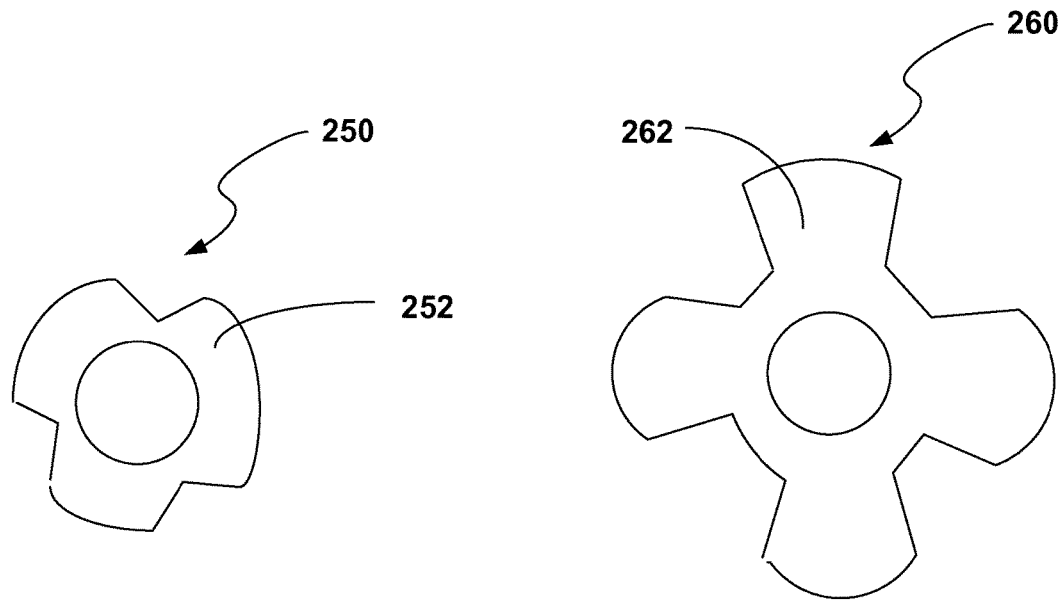
FIG. 2F
FIG. 2G

FLUID FILTRATION APPARATUS

CROSS-REFERENCE TO RELATED APPLICATIONS

This application claims priority to a United States provisional application filed on Mar. 15, 2013 and having Ser. No. 61/786,306.

FIELD OF THE INVENTION

The invention relates to devices and methods for fluid filtration. In certain embodiments, the invention is directed to optimizing methods of fluid filtration in combination with photocatalytic purification of pollutants and microbial contaminants.

BACKGROUND OF THE INVENTION

Clean, fresh air and water, free from pollutants, microbes and irritants is an important health concern for many people with compromised immune systems or those suffering from asthma, allergies, and other respiratory disorders or sensitivities. Outdoor air and water pollutants from car emissions, smog, transit systems, and industrial smoke create hazardous health concerns. More critically, indoor air quality poses a threat to health, especially those persons confined to hospitals, clinics, office buildings and transportation systems. For example, bacteria or microscopic particles carrying toxic substances may evade the body's air and fluid filtration systems allowing such toxic microbes or particles to penetrate deep into lung tissue resulting in absorption into the body of possibly toxic contaminants.

Indoor gaseous pollutants may also be a major risk factor to respiratory health. For example, volatile organic compounds (VOCs) are gases that are dispersed from plants, animals, microbes, fungi (molds), as well as in common cleaning solutions, paints, resins, synthetic fibers, and carpets. Building materials such as adhesives, paints, wall boards and ceiling tiles slowly emit the VOC, formaldehyde, which irritates mucous membranes compromising the immune system and exacerbating allergic reactions. Many VOCs such as benzene, are known carcinogens. In fact, studies have shown that prolonged exposure of VOCs in an indoor environment is related to an increase in the incidence of leukemia and lymphoma. Most indoor contaminants include not only VOCs but also organic materials such as dust mites, pet dander, bacteria, viruses, and fungi (mold). Fluid filtration systems have been developed for use in households, hospitals, or transportation systems. However, these systems merely trap these toxic particles and gases rather than destroy or deactivate the contaminants.

SUMMARY OF THE INVENTION

A device to optimize the filtration of a fluid flow via a filtration apparatus including optical fiber irradiation of a photocatalyst to destroy contaminants within the filtration apparatus is presented. The filtration apparatus includes a plurality of optical fibers in which one or more of the optical fibers of the plurality of optical fibers exhibits frustrated total internal reflection. The filtration apparatus further includes a photocatalyst disposed on or near the plurality of optical fibers and a light source interconnected to the plurality of optical fibers.

In an embodiment, the filtration apparatus includes a plurality of optical fibers in which one or more optical fibers of the plurality of optical fibers exhibits frustrated total internal reflection. The filtration apparatus also includes a photocatalyst disposed on the plurality of optical fibers. The filtration apparatus further includes a light source interconnected to the plurality of optical fibers.

In an embodiment, the filtration apparatus includes a plurality of optical fibers in which one or more optical fibers of the plurality of optical fibers exhibits frustrated total internal reflection. The filtration apparatus also includes a photocatalyst disposed adjacent to the plurality of optical fibers. The filtration apparatus further includes a light source interconnected to the plurality of optical fibers.

In an embodiment, the filtration apparatus includes a plurality of optical fibers in which one or more optical fiber of the plurality of optical fibers exhibits frustrated total internal reflection. The filtration apparatus further includes a light source interconnected to the plurality of optical fibers. In addition, the filtration apparatus includes a housing including a fluid intake portion and a fluid discharge portion. The filtration apparatus also includes an amplifier interconnected to the light source and at least one flow sensor disposed proximate to the fluid discharge portion of the housing. Additionally, the filtration apparatus includes a controller interconnected to the amplifier and the at least one flow sensor.

In an embodiment, a method of removing contaminants from a fluid is described. The method includes sensing a velocity of fluid flow through a filtration apparatus with at least one flow sensor. The filtration apparatus includes a plurality of optical fibers in which one or more optical fibers of the plurality of optical fibers exhibits frustrated total internal reflection, a photocatalyst coating disposed on or near the plurality of optical fibers, a light source interconnected to the plurality of optical fibers, an amplifier interconnected to the light source, and a housing comprising a fluid intake portion and a fluid discharge portion. The at least one flow sensor is disposed proximate to the fluid discharge portion of the housing. The filtration apparatus further includes a controller interconnected to the amplifier and the at least one flow sensor. The method also includes transmitting a signal from the at least one flow sensor to the controller and the controller responding to the at least one flow sensor signal by adjusting an intensity of the light source through the amplifier.

In an embodiment, an article of manufacture comprising non-transitory computer readable medium includes computer readable program code encoded to operate a filtration apparatus. The filtration apparatus includes a plurality of optical fibers in which one or more optical fibers of the plurality of optical fibers exhibits frustrated total internal reflection. The filtration apparatus also includes a photocatalyst disposed on or near the plurality of optical fibers, a light source interconnected to the plurality of optical fibers, and an amplifier interconnected to the light source. The filtration apparatus further includes a housing comprising a fluid intake portion and a fluid discharge portion in which the at least one flow sensor disposed proximate to the fluid discharge portion of the housing and a controller interconnected to the amplifier and the at least one flow sensor. The article of manufacture also includes the computer readable program code comprising a series of computer readable program steps to effect sensing a velocity of a fluid flow through the filtration apparatus with the at least one flow sensor, transmitting a signal from the at least one flow sensor to the controller, and responding to the at least one flow sensor signal by adjusting an intensity of the light source by the controller through the amplifier.

In an embodiment, a computer program product encoded in a non-transitory computer readable medium and usable to operate a filtration apparatus. The filtration apparatus includes a plurality of optical fibers, wherein one or more optical fibers of the plurality of optical fibers exhibits frustrated total internal reflection. The filtration apparatus further includes a photocatalyst disposed on or near the plurality of optical fibers, a light source interconnected to the plurality of optical fibers, and an amplifier interconnected to the light source. In addition, the filtration apparatus includes a housing including a fluid intake portion and a fluid discharge portion in which the at least one flow sensor is disposed proximate to the fluid discharge portion of the housing, and a controller interconnected to the amplifier and the at least one flow sensor. The computer program product existing code also including a computer readable program code which causes said one or more processors to sense a velocity of fluid flow through the filtration apparatus with the at least one flow sensor. The computer program product existing code further includes a computer readable program code which causes said one or more processors to transmit a signal from the at least one flow sensor to the controller. Additionally, the computer program product existing code further includes a computer readable program code which causes said one or more processors to signal the controller to respond to the at least one flow sensor signal by adjusting an intensity of the light source through the amplifier.

BRIEF DESCRIPTION OF THE DRAWINGS

The invention will be better understood from a reading of the following detailed description taken in conjunction with the drawings in which like reference designators are used to designate like elements, and in which:

FIGS. 2A-2G are cross sectional views of various optical fibers and photocatalyst coated optical fibers employed in a plurality of optical fibers within a filtration apparatus;

DETAILED DESCRIPTION OF PREFERRED EMBODIMENTS

Figure 1:
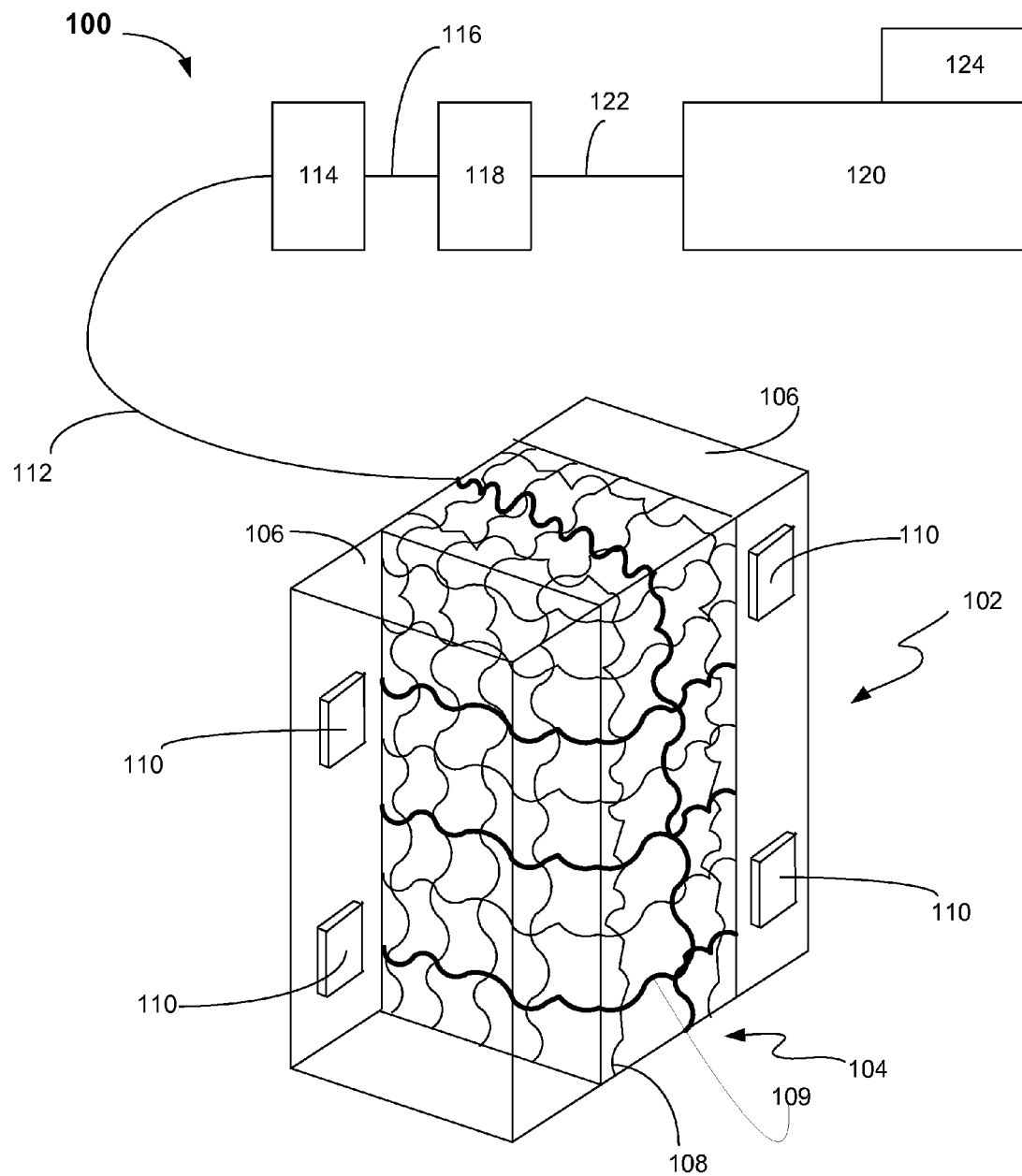
FIG. 1 illustrates a filtration apparatus including a photocatalyst coated plurality of optical fibers.

This invention is described in preferred embodiments in the following description with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of the invention may be combined in any suitable manner in one or more embodiments. In the following description, numerous specific details are recited to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

Photocatalytic oxidation, a form of photochemistry, is a chemical reaction caused by excitation of photocatalyst composition by electromagnetic radiation, such as and without limitation, light energy. Such light exposure in the presence of a photocatalyst can result in the break down of toxic organic molecules into harmless inert substances. More specifically, light energy causes excitation of one or more photocatalysts, wherein those excited photocatalysts transfer energy to ambient oxygen to form highly reactive oxidizing species which oxidize fluid borne contaminants. Integration of such technology into convenient filtration systems has broad air and water purification and deodorization applications for indoor environments. For example, environments including office buildings, transportation systems, aircraft cabins, residential buildings, healthcare and nursing facilities, and surgical theaters as well as clean rooms in the agricultural and food industry could benefit from such improved effectiveness and performance of this technology.

Embodiments of the invention relate to devices and methods for fluid filtration and purification of pollutants and microbial contaminants in a manner that destroys or deactivates the contaminants by light induced photocatalysis. In certain embodiments, the fluid filtration apparatus and methods described employ a controller and computer microprocessor including memory storing instructions to optimize the efficiency of the assembly, article of manufacture, computer program product, and methods. The devices and method embodiments disclosed herein may be used in a variety of applications, such as in a surgical environment, hospitals, geriatric care facilities, burn wards, transportation systems, airline carriers, residences, office buildings, nurseries, childcare facilities, and clean rooms in the agricultural and food industry.

FIG. 1. is an isometric schematic view illustrating a fluid filtration apparatus 100 according to an embodiment that comprises a filtration apparatus 102 including a plurality of optical fibers 104, and a housing 106. One or more optical fibers 108 of the plurality of optical fibers 104 are configured to exhibit frustrated total internal reflection, thereby emitting light along a length of one or more of the optical fibers 108. The housing 106 includes a fluid intake portion and a fluid discharge portion and at least one flow sensor 110 disposed proximate to the fluid intake portion and/or the fluid discharge portion of the housing 106.

A photocatalyst coating 109 is disposed onto one or more optical fibers of the plurality of optical fibers 104. The plurality of optical fibers 104 is interconnected to a light source 114 (via a communication link 112) that is controlled and interconnected through a communication link 116 by an amplifier 118 and a controller 120. The controller 120 is interconnected to the amplifier 118 through a communication link 122 and to at least one of flow sensors 110 through the communication link 112. The flow sensors 110 are configured to detect a volume of fluid flowing per second through the filtration apparatus 102 and to signal this information to the controller 120 and a computer microprocessor 124.

A filtration and purification action of the filtration apparatus 102 may be provided through photochemistry upon illumination of one or more of the optical fibers 108 by the light source 114 and excitation of photocatalyst 109. For example, when the photocatalyst coating is excited by radiation from the optical fiber, the photocatalyst generates excited oxygen moieties.

Such photocatalytic chemistry must be initiated by the illumination of the photocatalytic composition by a light source with a wavelength of light of sufficient intensity and wavelength to comprise energy that exceeds the photocatalyst species band gap energy. Additionally, a sufficient amount of the photocatalytic material must be photoactivated in order to oxidize the amount of contaminants present in the fluid flow (volume/second). This is achieved by configuring the controller 120 to adjust the intensity of the light source 114 as well as to modulate the energizing wavelength of light emitted via the amplifier 118 responsive to a signal from the at least one flow sensor 110. Thus, the controller 120 is configured to respond to a signal from the at least one flow sensor 110 by matching the amount of fluid (volume/second) flowing through the filtration apparatus 102 as detected by at least one flow sensor 110 with a corresponding intensity and duration of light energy emitted by the light source 114 as required by the specific photocatalyst species for activation. The controller 120 is further configured to subsequently adjust the duration, the energizing wavelength, as well as the intensity of light emitted by the light source 114 via the amplifier 118 to the values corresponding to the amount of fluid flow detected by the at least one flow sensor 110. It is these responsive adjustments by the controller 120 (via amplifier 118) that provide for sufficient activation of the photocatalyst coating the plurality of optical fibers 104 to cause oxidation and subsequent degradation of at least one contaminant of the fluid flow entering the housing 106 and the filtration apparatus 102.

In various embodiments, the photocatalyst coating of one or more of the optical fibers 108 comprises a composition including one or more titanium oxide moieties, a substituted photocatalyst selected from the group consisting of substituted Acetonaphthones, substituted Acetophenonse, substituted Acridines, substituted Anthracenes, substituted Anthraquinones, substituted Anthrones, substituted Azulenes, substituted Benzils, substituted Benzophenones, substituted Benzopyranones, substituted Benzoquinones, substituted Flavones, substituted Camphoroquinone, substituted Chrysenes, substituted 7-Dehydrocholesterols, substituted Ergosterols, substituted Fluorenes, substituted Fluorenones, substituted Eosins, substituted Fluoresceins, substituted Phloxines, substituted Rose Bengals, substituted Erythrosins, substituted Indoles, substituted Naphthalenes, substituted Phenanthrenes, substituted Phenazines, substituted Thionines, substituted Azures, substituted Toluidine Blue, substituted Methylene Blues, substituted Pyrenes, substituted Quinoxalines, substituted Retinals, substituted Riboflavins, substituted Rubrenes, substituted Bacteriochlorophylls, substituted Chlorophylls, substituted Pheophytins, substituted Pheophorbides, substituted Protochlorophylls, substituted Coproporphyrins, substituted Fullerenes, substituted Porphyrins, substituted Metallo Porphyrins, substituted Porphines, substituted Rubrenes, titanium dioxide, titanium dioxide-based photocatalysts, zinc oxide, strontium titanate, tin dioxide, niobium pentoxide, ferrous oxide, tetrachloroethylene, triethylamine, substituted phythalocyanine complexes, substituted porphyrin complexes, and substituted Phthalocyanines.

In certain embodiments, the photocatalyst coating may be comprised of a photocatalytic material in a layer formed on the surface of one or more optical fibers 108.

In certain embodiments, the photocatalytic coatings or layers comprise a thickness of about 100 nm to about 50 μm. In certain embodiments, the photocatalytic coatings or layers comprise a thickness of about 1 μm to about 50 μm. In certain embodiments, the photocatalytic coatings or layers comprise a thickness of about 1 μm to about 25 μm. In certain embodiments, the photocatalytic coatings or layers comprise a thickness of about 1 μm to about 20 μm. In certain embodiments, the photocatalytic coatings or layers comprise a thickness of about 1 μm to about 15 μm. In certain embodiments, the photocatalytic coatings or layers comprise a thickness of about 1 μm to about 10 μm. In certain embodiments, the photocatalytic coatings or layers comprise a thickness of about 5 μm to about 10 μm. In certain embodiments, the photocatalytic coatings or layers comprise a thickness of about 1 μm to about 5 μm. In certain embodiments, the photocatalytic coatings or layers comprise a thickness of about 2 μm to about 4 μm. In certain embodiments, the photocatalytic coatings or layers comprise a thickness of r about 1 μm to about 3 μm.

Figure 2A:
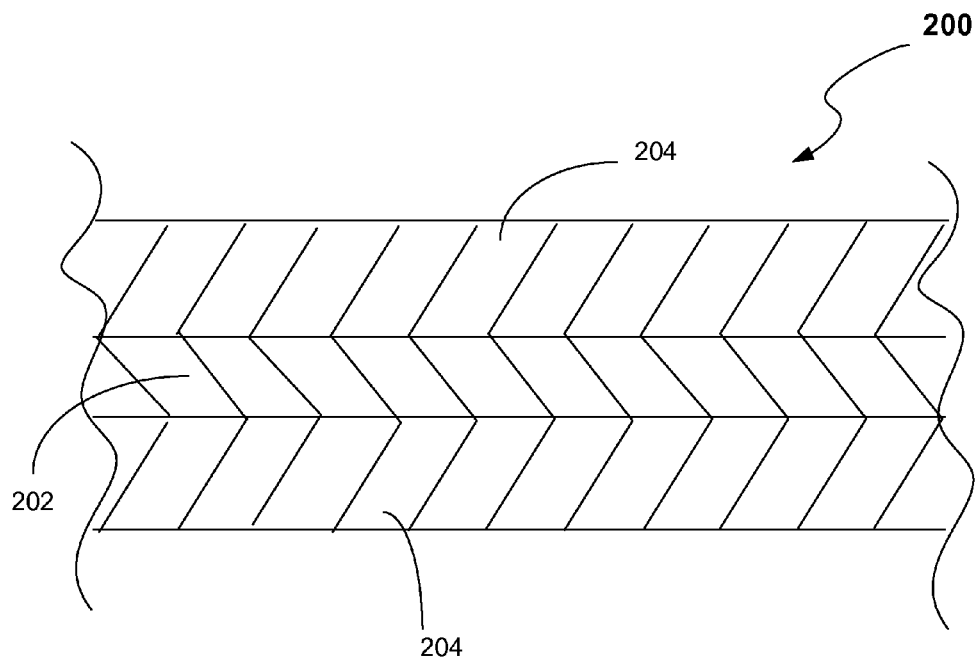
Figure 2B:
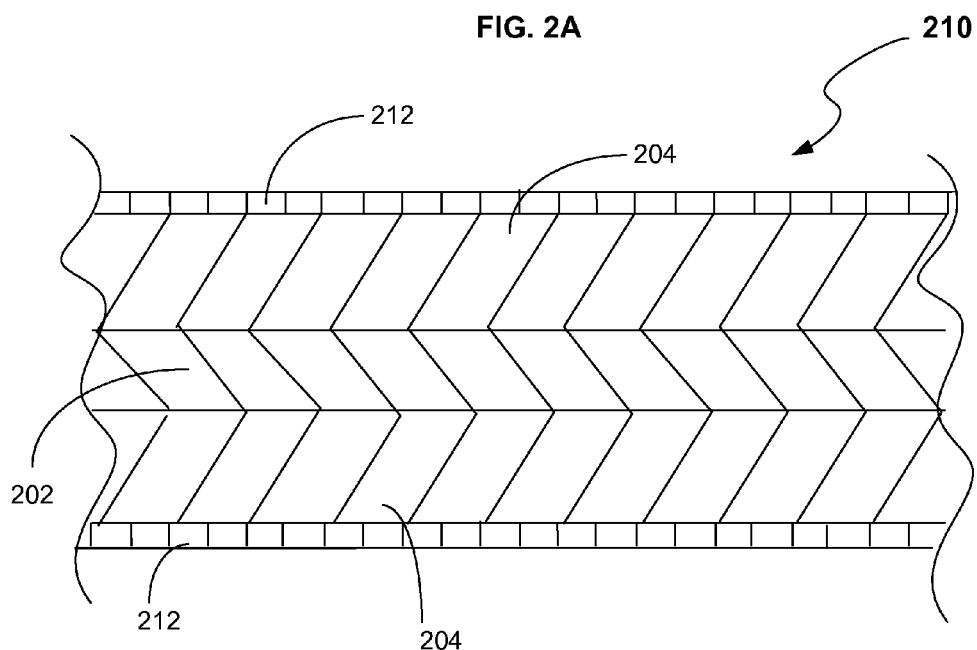

FIG. 2B illustrates an embodiment in which a single layer of photocatalyst coats the optical fiber. In other embodiments, two or more layers, or multiple layers of photocatalyst may coat the one or more optical fibers.

One or more of the optical fibers 108 comprises a flexible translucent or transparent fiber that functions to transmit light between the light source 114 and the photocatalyst coating material. The optical fibers 108 may be made of glass (silica), polymer, plastic, transparent material, translucent material, or in combinations of these materials in mixtures or layers. The optical fibers 108 are configured to propagate electromagnetic energy such as a wavelength of light down one or more of the optical fibers 108 of the plurality of optical fibers 104 from the light source 114 that is not confined to a core or a core and cladding of the optical fiber 108, and is of sufficient intensity and energizing wavelength to activate the photocatalyst disposed on the plurality of optical fibers 104.

FIGS. 2A-2F are cross sectional views of various optical fibers and photocatalyst coated optical fibers that may be employed a plurality of optical fibers within a filtration apparatus, according to different embodiments. FIGS. 2A and 2B are cross sectional views of an optical fiber 200 and a photocatalyst coated optical fiber 210. One or more optical fibers of the plurality of optical fibers may exhibit a uniform or a non-uniform radial distribution of the refractive index. For example, as shown in FIG. 2A, optical fiber 200 may include a core 202 surrounded by a cladding 204 with a lower index of refraction than that of the core 202. Such a configuration of refraction indices will maintain light within the core 202 by total internal reflection. However, for photocatalysis and the subsequent degradation (destruction) of airborne contaminants to occur, the photocatalyst coating 212 (shown in FIG. 2B) of the photocatalyst coated optical fiber 210 must be illuminated with a wavelength of light of sufficient intensity and energized wavelength so as to possess energy that exceeds the photocatalyst band gap energy. Such illumination of the photocatalyst may enable the photocatalyst to convert organic compounds in the airborne contaminants into harmless water vapor and carbon dioxide.

Figure 2C:
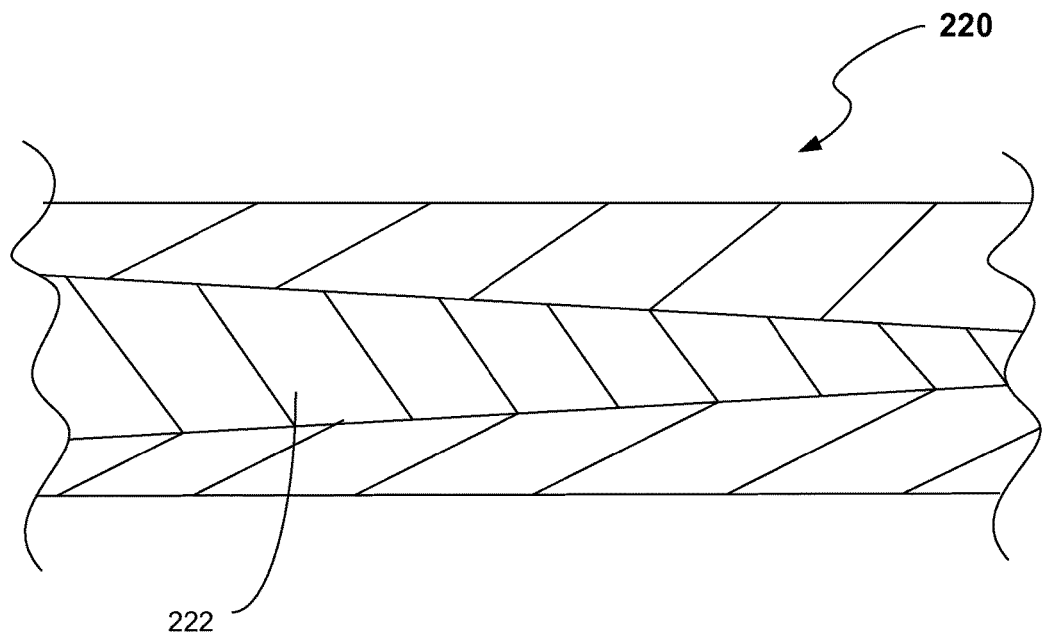
Figure 2D:
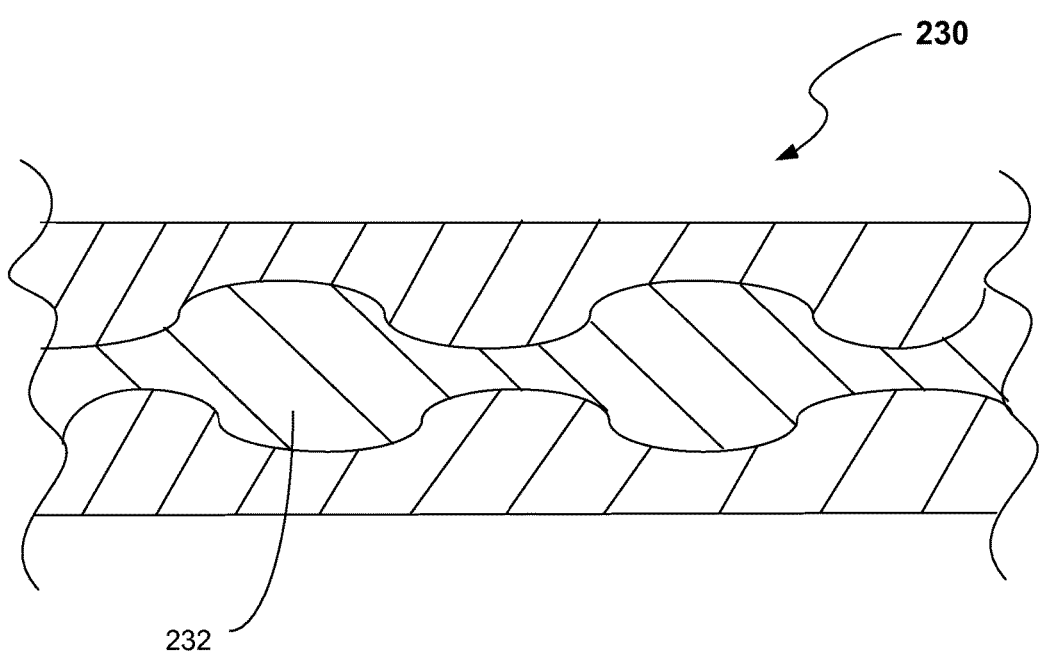

Thus, optical fibers such as those in the photocatalyst coated plurality of optical fibers 104 (shown in FIG. 1) may be engineered to emit light along the longitudinal axis of the optical fibers. This may be achieved by enabling frustrated total internal reflection for at least one of the optical fibers in the photocatalyst coated plurality of optical fibers 104. For example, optical fibers in the plurality of optical fibers 104 may be specifically designed such that the light intensity (at a wavelength sufficient to activate the photocatalyst) is not strongly confined within the optical fiber's core, thereby emitting light as it propagates along the length of the fiber. Alternatively, or in addition, as shown in FIG. 2C, an optical fiber 220 in the photocatalyst coated plurality of optical fibers 104 may be structured to have a core 222 with a diameter that varies as a function of the length of the fiber. Such variation may be random or according to a predetermined function as shown in FIGS. 2C and 2D. In another embodiment, one or more of the optical fibers 108 of the photocatalyst coated plurality of optical fibers 104 may include a functional form of a radial distribution of the refractive index. For example, one or more of the optical fibers 108 may include a functional form of a radial distribution selected from the group consisting of a step-like functional form, a monotonic functional form and a quadratic functional form.

Referring again to FIG. 2A, the optical fibers comprise the core 202 and the cladding 204. The core 202 and the cladding 204 may be made of the same material or of different materials. The material or materials chosen for the core and cladding should enable the propagation of electromagnetic energy down the length of the optical fiber such that one or more of the optical fibers glows with light and exhibits frustrated total internal reflection. For example, the electromagnetic energy may propagate down the length of the optical fiber such that the energy or wavelength of light is not confined to the combination of the core and cladding of one or more of the optical fibers but is allowed to emit light from at least a portion of the surface of one or more optical fibers of the plurality of optical fibers. Selection of such materials will allow for the emission of light along the longitudinal axis of one or more optical fibers 108 of the plurality of optical fibers 104 and permit the illumination of the photocatalyst coating. For example, the core 202 and the cladding may both be made of glass, polymer, resin, or of any translucent or transparent suitable material. Alternatively, the core 202 may be made of glass and the cladding of some non-glass material such as a polymer, resin, or other translucent or transparent suitable material. In another embodiment, the core 202 may be made of a polymer while the cladding may be made of glass, resin, or other translucent or transparent suitable non-polymeric material.

In another example, as shown in FIG. 2E, a surface of an optical fiber 240 in the plurality of optical fibers may be treated to produce an irregular surface of the cladding material 242 and enable light emission along the length of the fiber. In other embodiments, as shown in cross sections FIGS. 2F and 2G, the outer surface of the cladding 252 and 262 of optical fibers 250 and 260 may be grooved along the length of the fiber to facilitate light emission. In an embodiment, the plurality of optical fibers within the filtration apparatus are woven of optical fibers at least some of which are bent at a radius exceeding the critical radius for the wavelength of light necessary for the activation of the photocatalyst species. Bending of the optical fibers at such a radius enables light emission from the optical fibers and subsequent activation of the photocatalyst.

Although the plurality of optical fibers 104 are illustrated in FIG. 1 in a grid-like configuration, in a related embodiment the plurality of optical fibers 104 may be configured in two or three dimensions, in a mesh, a plurality, a grid, a honeycomb structure, a woven structure, a fin-like structure, a filamentous structure, or other suitable configuration in which the optical fibers 108 may form the plurality of optical fibers 104. For example, in an embodiment, the optical fibers 108 are intertwined and/or woven.

During operation of the fluid filtration apparatus 100, fluid flow is directed into the housing 106. Upon entry of the fluid flow into the housing 106, at least one flow sensor 110 detects a volume of fluid flow per second. Sensing this velocity of airflow, at least one flow sensor 110 transmits a signal indicating this information to the controller 120 and the microprocessor 124. In response to the signal from at least one flow sensor 110, the controller 120 and the microprocessor adjust an intensity of the light source 114 through the amplifier 118.

Figure 3A:
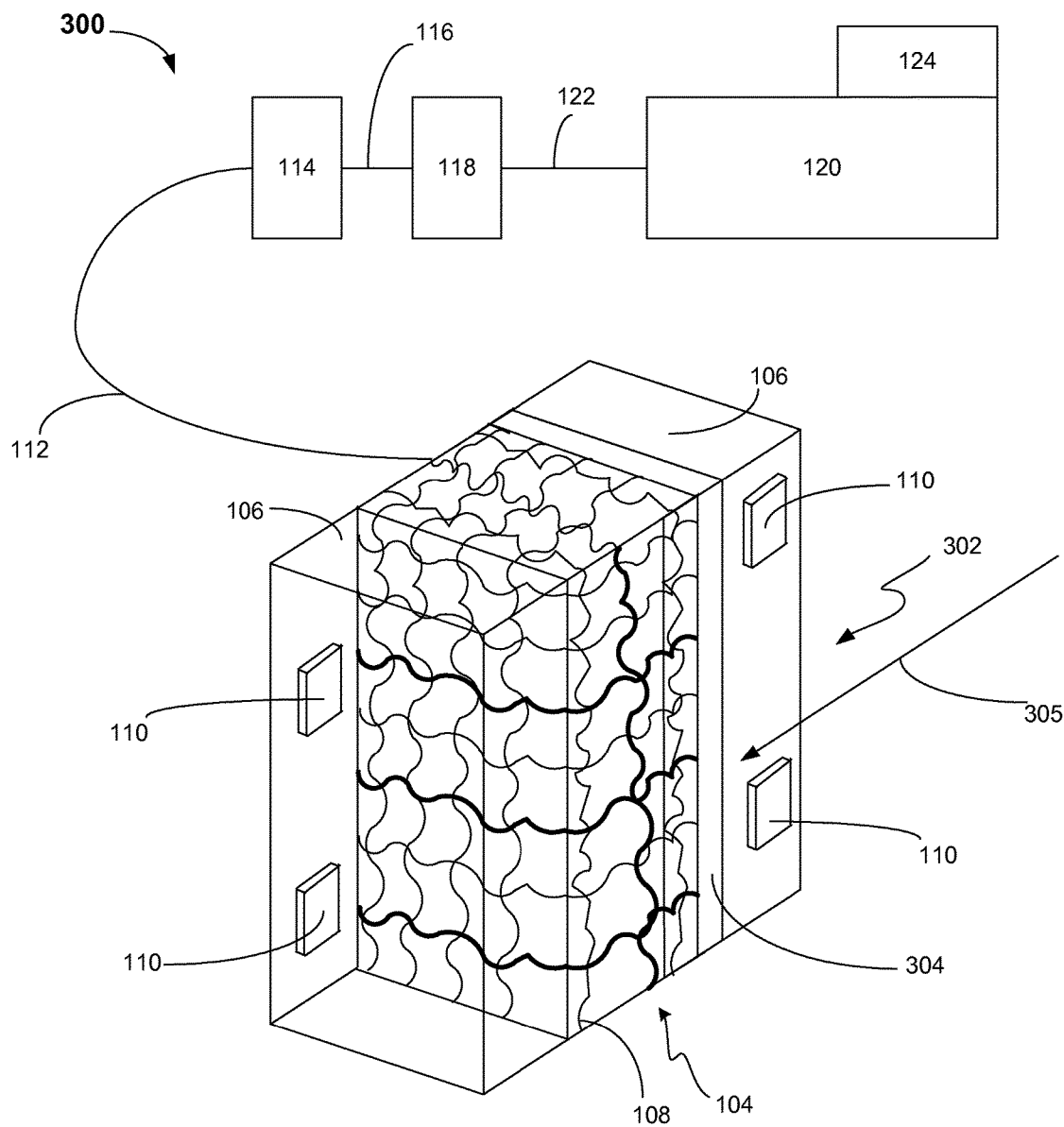
FIG. 3A illustrates a filtration apparatus including a plurality of optical fibers, a photocatalyst composition, and a fluid filtration medium.

A fluid filtration medium may be added to the fluid filtration apparatus 100 to provide for the filtration of airborne solid particulates. For example, FIG. 3A illustrates an isometric schematic view of a fluid filtration apparatus 300. In addition to the elements shown in FIG. 1, fluid filtration apparatus 300 further includes a fluid filtration medium 304 within a filtration apparatus 302. The fluid filtration medium 304 removes solid contaminating particulates such as microbes, viruses, dust, dirt, spores, fungi, or pollen from the fluid flow 305 through the filtration apparatus 302.

The fluid filtration medium 304 may comprise at least one of foam, paper, pleated paper, cotton, cloth, nylon, a woven polymer, or fiberglass filter elements. The fluid filtration medium 504 may comprise a structure including at least one of a mesh, a grid, a honeycomb, a woven structure, a fan, a sheet, a layered structure, a fin-like structure, a filamentous structure, or other suitable configuration.

The fluid filtration medium 304 may be configured to remove fluid borne solid particulates from the fluid flow before or after the fluid flow moves through the plurality of photocatalyst coated optical fibers 104 of the filtration apparatus 302. In an embodiment, the fluid filtration medium 304 may be disposable. For example, the filtration apparatus 302 may be configured to allow for removal of a clogged or otherwise ineffective fluid filtration medium and replacement with a new or unclogged fluid filtration medium. In an embodiment, one or more of the plurality of optical fibers 104 may be intertwined or otherwise configured to enable removal of fluid borne solid particulates from the fluid flow 305 of the filtration apparatus 302.

Electrostatic air cleaners have two main drawbacks. First, they can produce ozone, a known lung irritant and asthma trigger. While many units produce negligible levels of ozone, there are some brands and models on the market that exceed government safety standards. They may also produce ultra-fine particles from the reaction of the ozone with indoor chemicals (e.g., those from household cleaning products, paints, flooring or carpeting) that some people are sensitive to.

The second major drawback is the need to constantly wash the collector plates. The ability of the plates to attract particles decreases rapidly as they fill up, so they need to be cleaned frequently (e.g., weekly or even daily, depending on the levels of contaminants in the room) to keep the air cleaner working at maximum efficiency. Because the particles bond so tightly to the metal plates, vigorous scrubbing may be necessary to clean them completely, while the close spacing of the fixed plates in some models can make them a challenge to maintain.

Polarization is very different from ionization because polarized molecules are not charged. In addition and as those skilled in the art will appreciate, a polarized field does not produce any ozone, which occurs with ionizing. Ionized particles have either a positive or negative charge and are attracted to oppositely charged surfaces such as collector plates in precipitating air cleaners. Such charged particles have the ability to also collect on walls, ductwork, and clothes.

Figure 3B:
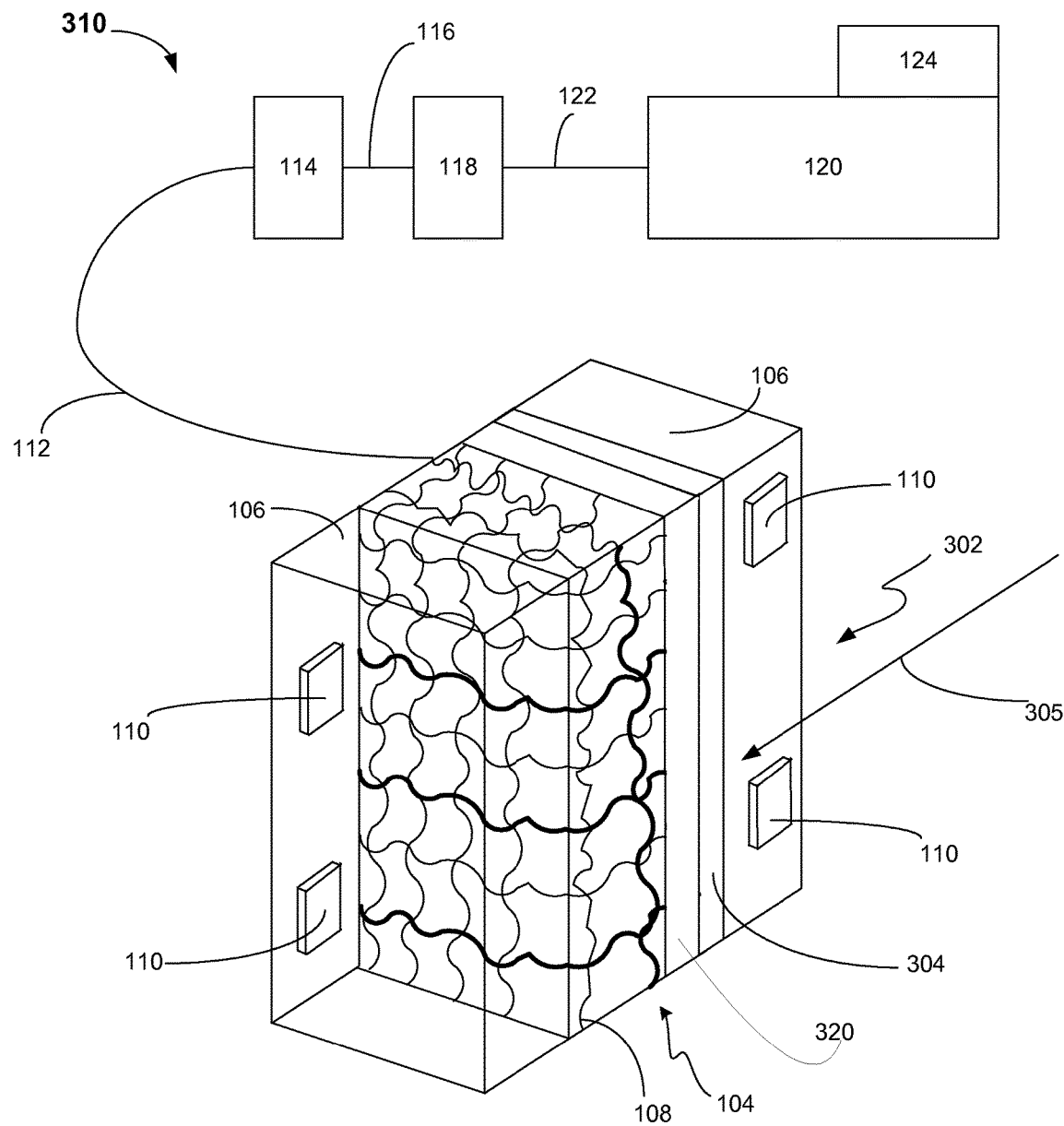
FIG. 3B illustrates a filtration apparatus including a plurality of optical fibers, a photocatalyst composition, a polarizing air cleaner unit, and a fluid filtration medium

Polarized particles are bi-polar which means that each molecule charge (at one end) and a negative charge (at the other end). Polarized particles are attracted to the other polarized particles that tend to float free and are recirculated through an HVAC system. Such agglomeration facilitates filtration. Referring to FIG. 3B, fluid filtration apparatus 310 further comprises a polarizing air cleaner 320. Highly efficient filtration devices that minimally impede fluid flow, polarizing air cleaners can provide for removal of fine particulate matter such as dust and smoke without generation of ozone.

The polarizing air cleaner 320 may be configured to remove fluid borne fine dust, dirt, and smoke particles from the fluid flow 305 before or after the fluid flow 305 moves through the plurality of photocatalyst coated optical fibers 104 or before or after the fluid flow 305 moves through the fluid filtration medium 304 of the filtration apparatus 302. In an embodiment, the polarizing air cleaner 320 may add to the efficiency of the filtration apparatus 302. For example, the fluid flow 305 may initially flow through the polarizing air cleaner 320 removing fine particulates (substantially sub-micron in size) of grit, dust, dirt, or smoke. The fluid flow 305 exiting the polarizing air cleaner 320 may next flow through the fluid flow medium 304 removing bacteria, viruses, microbes, and solid particulate matter too large to be captured by the polarizing air cleaner 320. Finally, the fluid flow 305 exiting the fluid flow medium 304 may flow through the plurality of photocatalyst coated optical fibers 104 where toxic organic molecules are subsequently broken down into harmless molecules. In such an embodiment, the polarizing air cleaner 320 and the fluid flow medium 304 provide two methods of solid particulate removal allowing for more efficient and thorough chemical toxin removal by the plurality of photocatalyst coated optical fibers 104. Additionally, such an embodiment may prevent the filtration apparatus 302 from clogging or diminishing the fluid flow 305 through the filtration apparatus 302.

In certain embodiments, fluid flow 305 first enters housing 106, then passes through filter medium 304, then passes through polarizing air cleaner 320, then passes through the matrix of optical fibers 104. In other embodiments, fluid flow 305 first enters housing 106, then passes through polarizing air cleaner 320, then passes through physical filtration medium 304, then passes through the matrix of optical fibers 104.

Figure 4A:
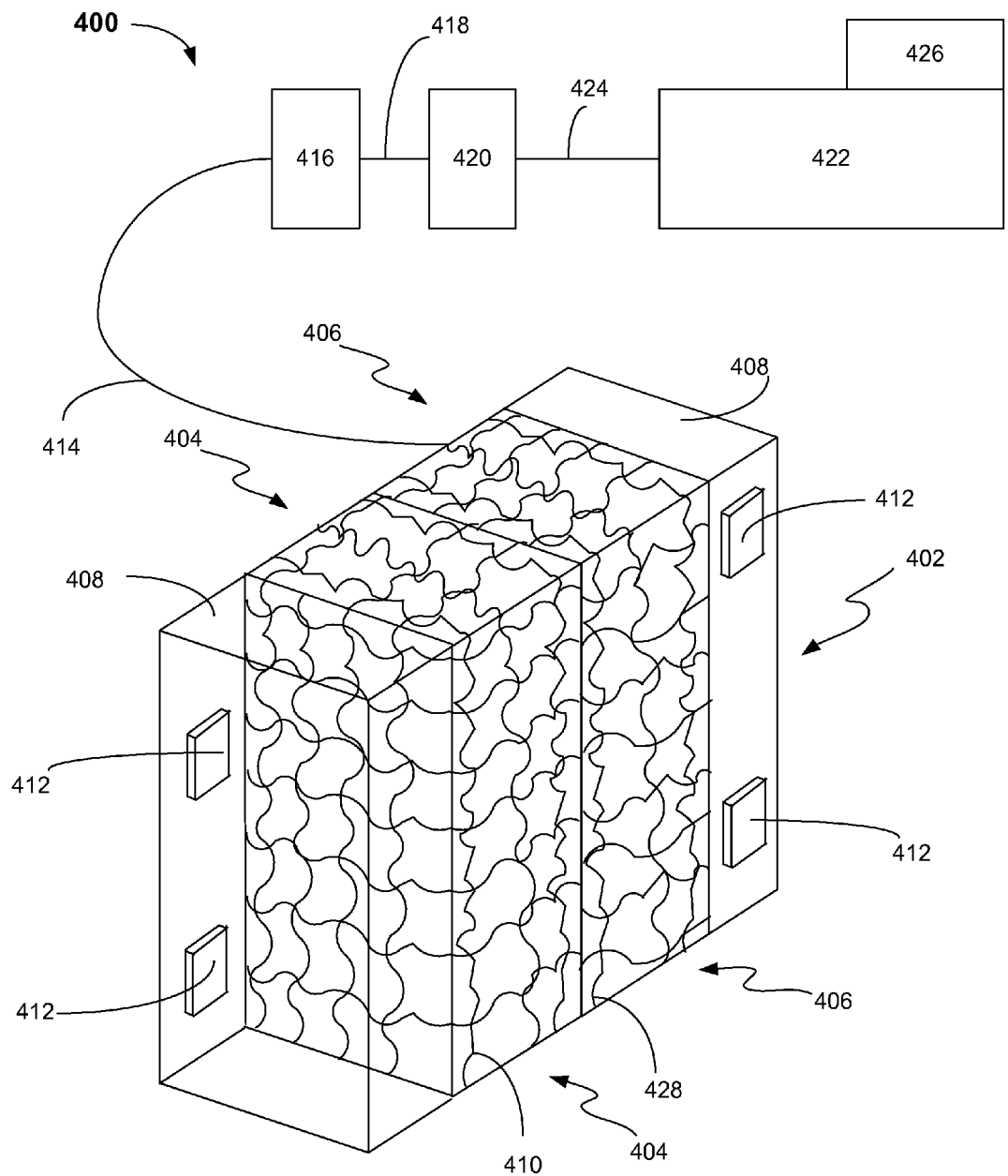
FIG. 4A illustrates a filtration apparatus including a plurality of optical fibers and a fabric comprising a plurality of photocatalyst coated fibers.

FIG. 4A is an isometric schematic view illustrating a filtration apparatus and system 400 according to an embodiment that comprises a filtration apparatus 402 including a plurality of optical fibers 404, a fabric 406 comprising a plurality of photocatalyst coated fibers, and a housing 408. One or more of the optical fibers 410 of the plurality of optical fibers 404 is configured to exhibit frustrated total internal reflection, thereby emitting light along the length of one or more of the optical fibers 410. The housing 408 includes a fluid intake portion and a fluid discharge portion and at least one flow sensor 412 disposed proximate to the fluid intake and/or the fluid discharge portion of the housing 408.

A photocatalyst coating covers one or more of the plurality of fibers of the fabric 406 enabling photocatalysis of airborne contaminants by illumination of the photocatalyst coated fabric 406 by the adjacent plurality of optical fibers 404. The plurality of optical fibers 404 is interconnected to the amplifier 420 via a communication link 414 with a light source 416 that is controlled through communication link 418 by an amplifier 420 and a controller 422. The controller 422 is interconnected to the amplifier 420 through a communication link 424 and to at least one flow sensor 412 through the communication link 414. The at least one flow sensor 412 is configured to detect a volume of fluid flowing per second through the filtration apparatus 402 and to signal this information to the controller 422 and to a computer microprocessor 426.

The at least one flow sensor 412 is configured to signal the volume of fluid flowing per second through the housing 408 and the filtration apparatus 402 to the controller 422 and a computer microprocessor 426. The controller 422 is configured to adjust the intensity of the light source 416 as well as to modulate the wavelength of light emitted via the amplifier 420 responsive to the signal from the at least one flow sensor 412 and to the photocatalyst species used. Thus, the controller 422 is configured to respond to a signal from the at least one flow sensor 412 by matching the amount of air (volume/second) flowing through the filtration apparatus 402 as detected by the at least one flow sensor 412 with a corresponding intensity and duration of electromagnetic energy emitted by the light source 416 as required by the specific photocatalyst species. The controller 422 is further configured to subsequently adjust the duration, the energizing wavelength, as well as the intensity of light emitted by the light source 416 via the amplifier 420 to the values corresponding to the amount of fluid flow detected by the at least one flow sensor 412. It is these responsive adjustments by the control 134 422 (and amplifier 420) that provide for sufficient activation of the photocatalyst coating the plurality of optical fibers 404 to cause oxidation and subsequent degradation of at least one contaminant of the fluid flow entering the housing 408 and the filtration apparatus 402

In various embodiments, the photocatalyst coating of one or more of the fibers of the fabric 406 may comprise any of the materials described herein and as previously described for the photocatalyst coating composition of the plurality of optical fibers 104 as shown in FIGS. 1 and 3.

One or more of the optical fibers 410 within the plurality of optical fibers 404 may comprise any of the materials described herein and as previously described for the optical fibers 108 of the plurality of optical fibers 104 as shown in FIGS. 1 and 3. As also described with regard to the optical fibers 108, one or more of the optical fibers 410 are configured to propagate a wavelength of light down one or more of the optical fibers 410 of the plurality of optical fibers 404 from the light source 416 that is not confined to a core or a core and cladding (as shown in FIGS. 2A-2G) of the optical fiber 410, and is of sufficient intensity and energizing wavelength to activate the photocatalyst disposed on the plurality of optical fibers 404.

Figure 4B:
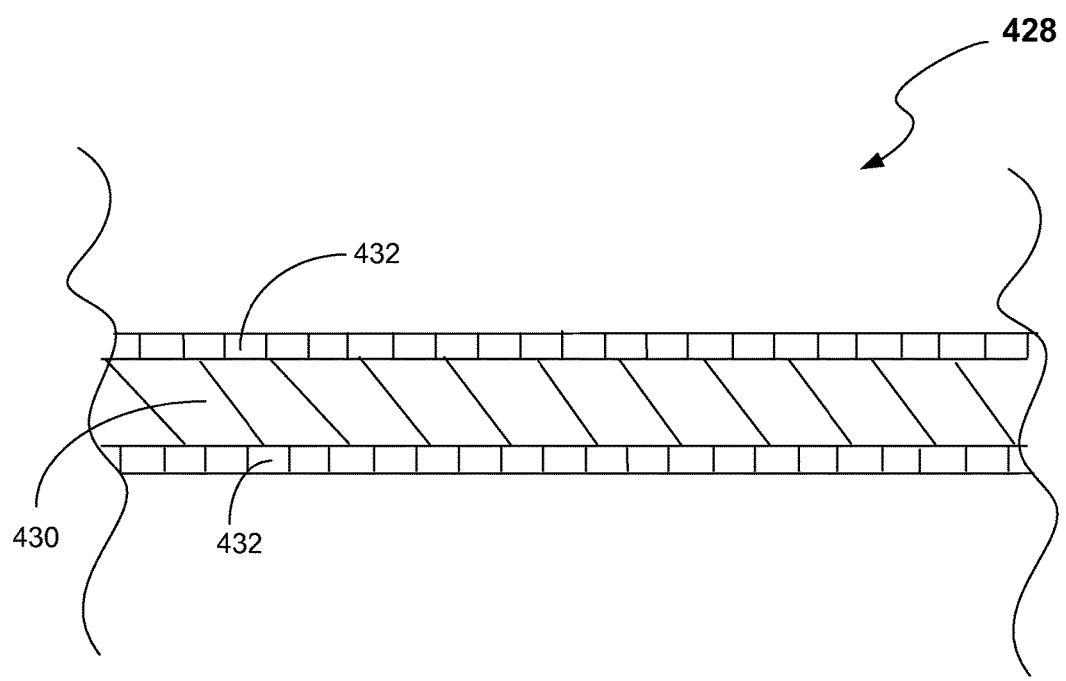
FIG. 4B illustrates a cross-sectional view of the photocatalyst coated fiber 428.

FIG. 4B illustrates a cross-sectional view of the photocatalyst coated fiber 428, according to an embodiment. The photocatalyst coated fiber 500 includes a core 502 comprising at least one of a polymer, a resin, fiberglass, glass, plastic, ceramic, metal, aluminum, copper, steel, stainless steel, or other suitable base material. A composition of photocatalyst coating 504 of the fiber 500 may comprise any of the materials, dimensions, and weight percentages described previously with regard to the photocatalyst coated plurality of optical fibers 104 and set forth herein. Although the plurality of optical fibers 404 and the fabric 406 are illustrated in FIG. 4A in a grid-like configuration, in a related embodiment the plurality of optical fibers 404 and the fabric 406 may be configured in two or three dimensions, in a mesh, a network, a grid, a honeycomb structure, a woven structure, a fin-like structure, a filamentous structure, or other suitable configuration. In an embodiment, one or more of the optical fibers 410 of the plurality of optical fibers 404 and one or more of the fibers 428 of the fabric 406 are intertwined and/or woven.

In an alternative embodiment, both the fabric 406 and the plurality of optical fibers 404 may be coated with photocatalyst. In an embodiment, two layers or three or more layers of pluralities of optical fibers and pluralities of photocatalyst non-optical fibers may be used in the filtration apparatus 402 in combination without limitation. For example, a photocatalyst coated fabric may be disposed between two pluralities of optical fibers.

Figure 5:
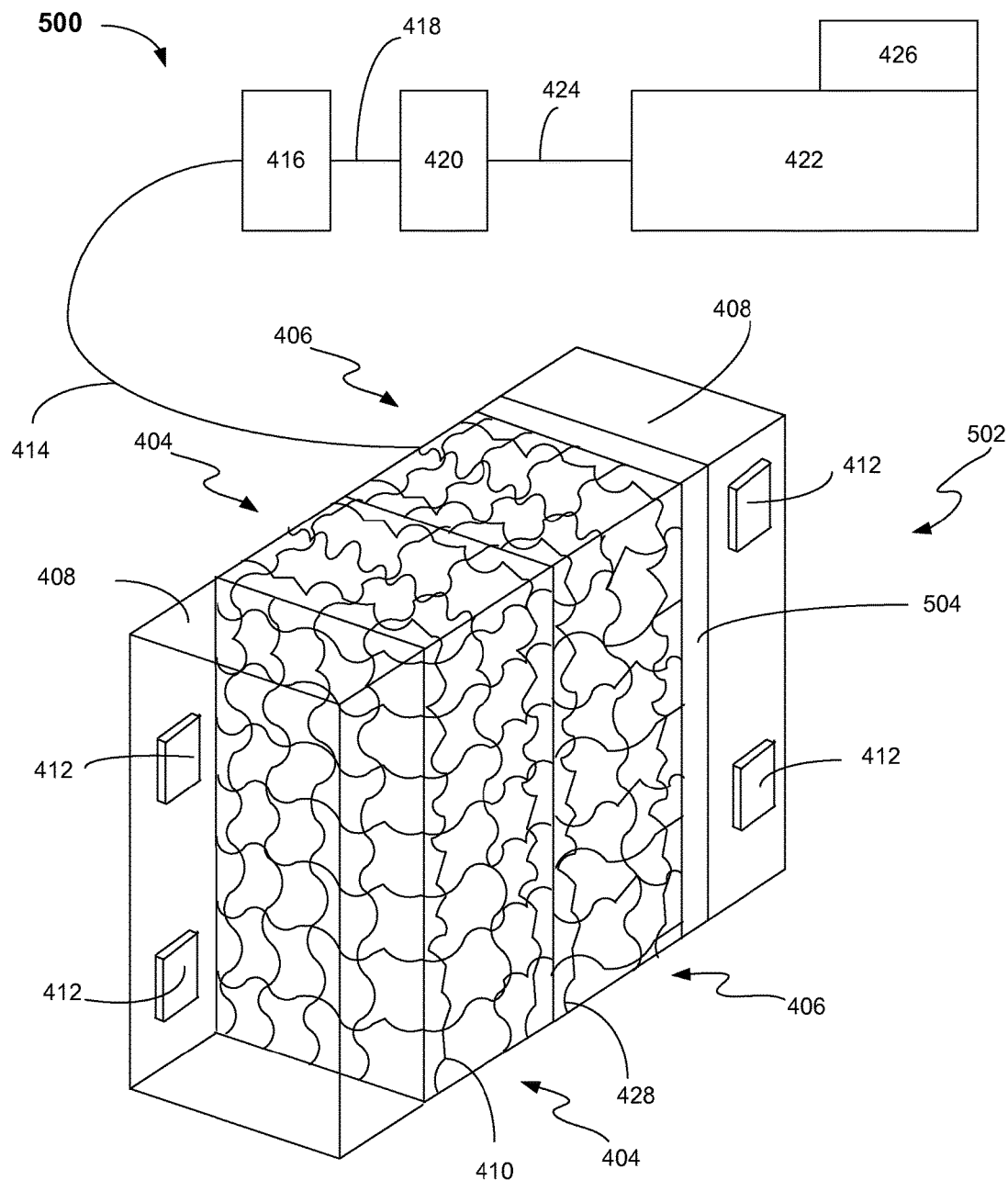
FIG. 5 illustrates a filtration apparatus comprising a plurality of optical fibers, a fabric comprising a plurality of photocatalyst coated fibers, and a fluid filtration medium.

A fluid filtration medium may be added to the fluid filtration apparatus 400 to provide for the filtration of airborne solid particulates. For example, FIG. 5 illustrates an isometric schematic view of an fluid filtration apparatus and system 500. Similar to the fluid filtration apparatus shown in FIG. 4A in a related embodiment, fluid filtration apparatus and system 500 further includes the fluid filtration medium 504 within a filtration apparatus 502. The fluid filtration medium 504 allows for the removal of solid contaminating particulates such as microbes, viruses, dust, dirt, spores, fungi, or pollen from the fluid flow through a fluid filtration medium 504. The fluid filtration medium 504 may include a membrane filter material comprising at least one of foam, paper, pleated paper, cotton, cloth, nylon, a woven polymer, or fiberglass filter elements. The fluid filtration medium 504 may comprise a structure including at least one of a mesh, a network, a grid, a honeycomb, a woven structure, a fan, a sheet, a layered structure, a fin-like structure, a filamentous structure, or other suitable two or three dimensional structure.

Referring to FIG. 5, a fluid filtration medium 504 is shown adjacent to the fabric 406 such that the fabric 405 is disposed between the fluid filtration medium 504 and the plurality of optical fibers 404. FIG. 5 illustrates the fluid filtration medium 504 as configured to remove airborne solid particulates from the airflow before the fluid flow enters the photocatalyst coated fabric, the fluid filtration medium 504 may be configured to remove airborne solid particulates from the fluid flow after the fluid flow moves through the fabric 406 of the filtration apparatus 502. In an embodiment, the fluid filtration medium 504 may be disposed between the photocatalyst coated fabric 406 and the plurality of optical fibers 404. In an embodiment, the plurality of optical fibers 404 may be disposed between the photocatalyst coated fabric 406 and the fluid filtration medium 504. In an embodiment, the photocatalyst coated fabric 406 may be disposed between the fluid filtration medium 504 and the plurality of optical fibers 404. In an embodiment, the fluid filtration medium 504 may comprise one layer, or two or more layers of the membrane filter material. In an embodiment, the fluid filtration medium 504 may be disposable. For example, the filtration apparatus 502 may be configured to allow for removal of a clogged or otherwise ineffective fluid filtration medium and replacement with a new or unclogged fluid filtration medium.

In certain embodiments, fluid flow first enters a housing, such as housing 106/406, then passes through a filter medium 304/504, then passes through an ESD 320, then passes through a matrix of optical fibers 404, then passes through a matrix of photocatalyst covered fabric 406. In certain embodiments, fluid flow first enters a housing, such as housing 106/406, then passes through an ESD 320, then passes through a filter medium 304/504, then passes through a matrix of optical fibers 404, then passes through a matrix of photocatalyst covered fabric 406.

In certain embodiments, fluid flow first enters a housing, such as housing 106/406, then passes through a filter medium 304/504, then passes through an ESD 320, then passes through a combined matrix of optical fibers 404 and photocatalyst covered fabric 406. In certain embodiments, fluid flow first enters a housing, such as housing 106/406, then passes through an ESD 320, then passes through a filter medium 304/504, then passes through a combined matrix of optical fibers 404 and photocatalyst covered fabric 406.

While the preferred embodiments of the present invention have been illustrated in detail, it should be apparent that modifications and adaptations to those embodiments may occur to one skilled in the art without departing from the scope of the present invention.

I claim:

1. A fluid filtration apparatus comprising:
   a plurality of optical fibers each having a length, the plurality of optical fibers comprising a first assembly, wherein one or more of the plurality of optical fibers exhibits frustrated total internal reflection, thereby emitting light along the length of one or more of the optical fibers;
   a photocatalyst disposed on said plurality of optical fibers;
   a light source interconnected to the plurality of optical fibers;
   a second assembly comprising a fabric including a plurality of fibers wherein one or more of the plurality of fibers comprises said photocatalyst disposed thereon;
   a third assembly comprising a fluid filtration medium, wherein the second assembly is disposed between the first assembly and the third assembly.

2. The fluid filtration apparatus of claim 1, further comprising:
   a housing comprising a fluid intake portion and a fluid discharge portion;
   an amplifier interconnected to the light source;
   at least one flow sensor disposed proximate to the fluid discharge portion of the housing; and
   a controller interconnected to the amplifier and the at least one flow sensor.

3. The fluid filtration apparatus of claim 2, wherein the controller is configured to adjust the intensity of the light source via the amplifier responsive to a signal from the at least one flow sensor.

4. The fluid filtration apparatus of claim 1, wherein the plurality of optical fibers propagate electromagnetic energy therein from the light source, wherein the electromagnetic energy is not confined to a core and cladding of one or more of the optical fibers.

5. The fluid filtration apparatus of claim 4, wherein the electromagnetic energy is of sufficient intensity and energizing wavelength to activate the photocatalyst disposed on the plurality of optical fibers.

6. The fluid filtration apparatus of claim 1, wherein the optical fibers of the plurality of optical fibers are intertwined.

7. The fluid filtration apparatus of claim 1, wherein the light source is integral to the plurality of optical fibers.

8. The fluid filtration apparatus of claim 1, wherein one or more of the optical fibers of the plurality of optical fibers includes a uniform radial distribution of the refractive index.

9. The fluid filtration apparatus of claim 1, wherein one or more of the optical fibers of the plurality of optical fibers includes a non-uniform radial distribution of the refractive index.

10. The fluid filtration apparatus of claim 1, wherein one or more of the optical fibers of the plurality of optical fibers includes a functional form of a radial distribution of the refractive index selected from the group consisting of a step-like functional form, a monotonic functional form, and a quadratic functional form.

11. The fluid filtration apparatus of claim 1, wherein one or more of the optical fibers of the plurality of optical fibers includes a glass core having a diameter that varies as a function of a length of the optical fiber.

12. The fluid filtration apparatus of claim 1, wherein the photocatalyst coating comprises at least one of titanium dioxide, zinc oxide, strontium titanate, tin dioxide, niobium pentoxide, ferrous oxide, substituted phythalocyanine complexes, and substituted porphyrin complexes.

13. The fluid filtration apparatus of claim 1, wherein the first assembly is disposed between the second assembly and the third assembly.

14. The fluid filtration apparatus of claim 1, wherein the third assembly is disposed between the first assembly and the second assembly.

15. The fluid filtration apparatus of claim 1, wherein the fabric comprises a plurality of polymer fibers including a photocatalyst disposed thereon.

16. The fluid filtration apparatus of claim 1, wherein the first assembly comprises a plurality of optical fibers without a photocatalyst disposed thereon.

* * * * *